United States Patent [19]

Berger et al.

[11] Patent Number: 5,461,057
[45] Date of Patent: Oct. 24, 1995

[54] HYDRO-ETHANO-INDENO-PYRIDINES

[75] Inventors: Joel G. Berger, Cedar Grove; David J. Blythin, North Caldwell; Ronald J. Doll; Jonathan A. Pachter, both of Maplewood, all of N.J.

[73] Assignee: Schering Corporation, Kenilworth, N.J.

[21] Appl. No.: 303,244

[22] Filed: Sep. 8, 1994

[51] Int. Cl.$^6$ .................... C07D 221/18; A61K 31/435
[52] U.S. Cl. ................................. 514/289; 546/72
[58] Field of Search ................... 546/72; 514/289

[56] References Cited

U.S. PATENT DOCUMENTS

| 3,901,892 | 8/1975 | Clark et al. | 260/283 |
| 4,179,567 | 12/1979 | Clark et al. | 546/124 |

OTHER PUBLICATIONS

Entry No. 5643; "Mazindol"; p. 903; Merck Index 11th Ed; (1989) (8).

*Primary Examiner*—Johann Richter
*Assistant Examiner*—Laura L. Stockton
*Attorney, Agent, or Firm*—Eric S. Dicker; John J. Maitner; Matthew Boxer

[57] ABSTRACT

A compound of formula I

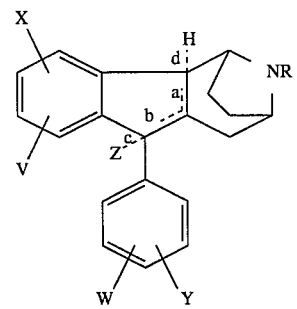

wherein X, V, W, Y, Z, R, a, b, c, and d are as described herein.

These compounds are useful in the treatment of tumors, allergies, bronchoconstriction and CNS diseases and conditions.

17 Claims, No Drawings

HYDRO-ETHANO-INDENO-PYRIDINES

SUMMARY OF THE INVENTION

The invention relates to compounds of the formula

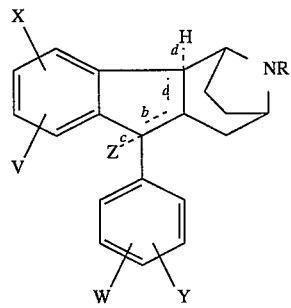

I wherein R is H; $(C_1-C_8)$alkyl; $(C_3-C_8)$cycloalkyl; $(C_3-C_8)$cycloalkyl; $(C_1-C_8)$alkyl; $(C_3-C_8)$alkenyl; and $(C_3-C_8)$alkynyl, with the proviso that the double bond in $(C_3-C_8)$alkenyl and the triple bond in $(C_3-C_8)$alkynyl must be separated from the nitrogen in the 2-position by at least one saturated carbon;

X, V, W and Y are each independently H, halogen, $NO_2$, CN, $(C_1-C_8)$alkyl, $O(C_1-C_8)$-alkyl, $S(C_1-C_8)$alkyl, $(C_3-C_8)$alkenyl; $(C_3-C_8)$alkynyl; hydroxy$(C_1-C_8)$alkyl; cyano$(C_1-C_4)$alkyl; $S(O)m(C_1-C_8)$-alkyl wherein m is 1 or 2; $NH_2$, OH, or $CF_3$;

W and Y on adjacent carbons can be

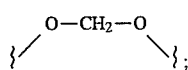

and a, b, c, and d are optionally chemical bonds with the proviso that when a is a bond, b is not a bond, c is a bond, d is not a bond, and Z is H;

and when b is a bond, a is not a bond, c is not a bond, and d is a bond;

and when a and b are not bonds, and c and d are bonds and Z is H or OH;

and when d is a bond, said bond is attached to H, and when d is not a bond, said H is not present;

and when c is not a bond, Z is not present; and stereoisomers thereof; and pharmaceutically acceptable salts thereof.

Preferred are compounds of the formula:

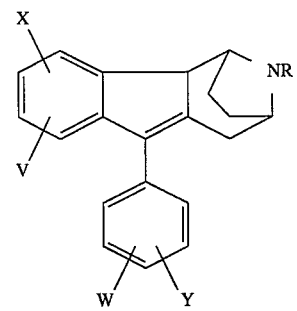

I''' wherein X, V, W, Y and R are as described herein.

Also preferred among the compounds of the invention are compounds of the formula:

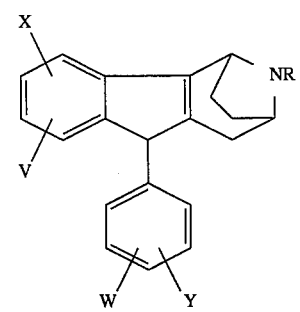

I'' wherein X, V, W, Y and R are as described herein.

Also preferred are compounds of the formula:

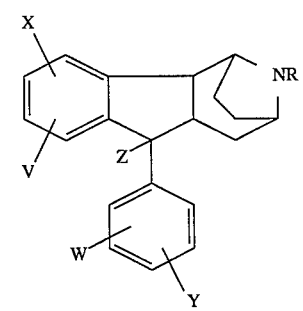

I$^{IV}$ wherein X, V, W, Y, Z and R are as described herein.

Also preferred are Compounds according to claim 1 wherein R is H.

Also preferred are compounds according to claim 1 wherein R is $CH_3$.

Also preferred are compounds according to claim 1 wherein W is H and Y is —$OCH_3$.

Also preferred are compounds according to claim 1 wherein no more than one of X, V, W and Y is halogen.

Also preferred are compounds of formula I with the proviso that when Z is OH, b and a are not bonds, and at least one of X and V are halogen, then neither W nor Y can be O—$(C_1-C_8)$alkyl, in the 4'-position.

Individual compounds of the invention are shown in the tables below. Formula XXX, in the DETAILED DESCRIPTION OF THE INVENTION below, gives the numbering of the positions on the rings of the compounds.

Exemplary of compounds of the invention of formula I are:

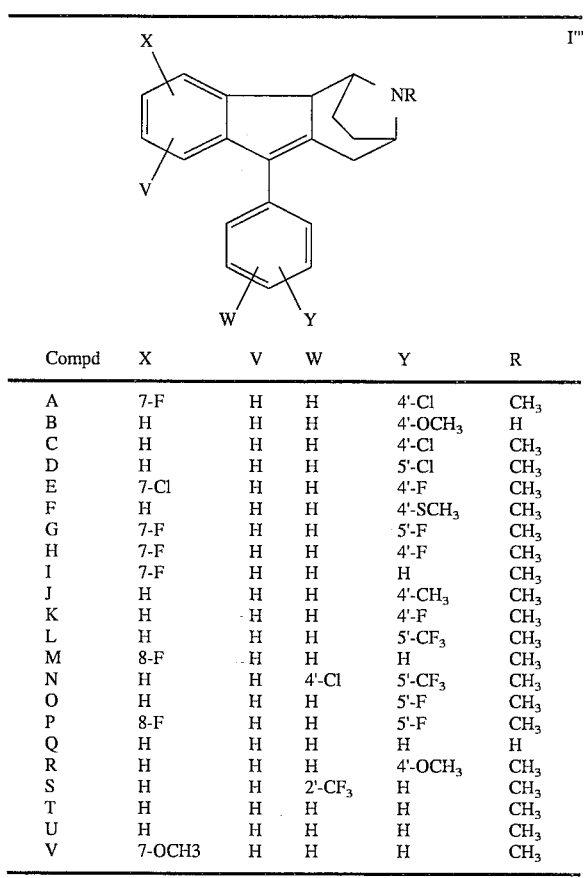

| Compd | X | V | W | Y | R |
|---|---|---|---|---|---|
| A | 7-F | H | H | 4'-Cl | CH₃ |
| B | H | H | H | 4'-OCH₃ | H |
| C | H | H | H | 4'-Cl | CH₃ |
| D | H | H | H | 5'-Cl | CH₃ |
| E | 7-Cl | H | H | 4'-F | CH₃ |
| F | H | H | H | 4'-SCH₃ | CH₃ |
| G | 7-F | H | H | 5'-F | CH₃ |
| H | 7-F | H | H | 4'-F | CH₃ |
| I | 7-F | H | H | H | CH₃ |
| J | H | H | H | 4'-CH₃ | CH₃ |
| K | H | H | H | 4'-F | CH₃ |
| L | H | H | H | 5'-CF₃ | CH₃ |
| M | 8-F | H | H | H | CH₃ |
| N | H | H | 4'-Cl | 5'-CF₃ | CH₃ |
| O | H | H | H | 5'-F | CH₃ |
| P | 8-F | H | H | 5'-F | CH₃ |
| Q | H | H | H | H | H |
| R | H | H | H | 4'-OCH₃ | CH₃ |
| S | H | H | 2'-CF₃ | H | CH₃ |
| T | H | H | H | H | CH₃ |
| U | H | H | H | H | CH₃ |
| V | 7-OCH3 | H | H | H | CH₃ |

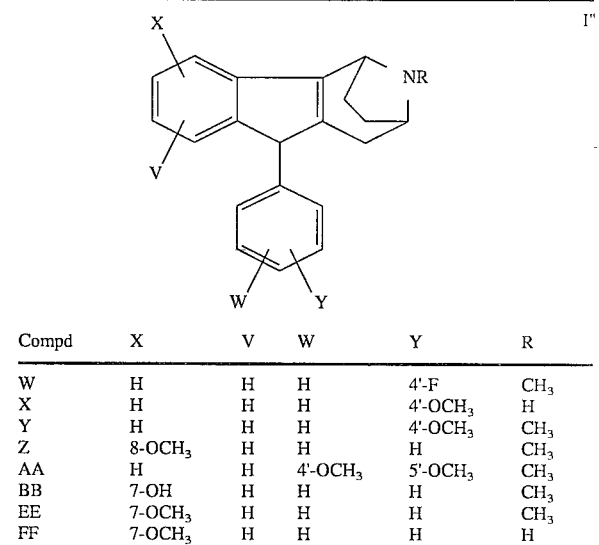

| Compd | X | V | W | Y | R |
|---|---|---|---|---|---|
| W | H | H | H | 4'-F | CH₃ |
| X | H | H | H | 4'-OCH₃ | H |
| Y | H | H | H | 4'-OCH₃ | CH₃ |
| Z | 8-OCH₃ | H | H | H | CH₃ |
| AA | H | H | 4'-OCH₃ | 5'-OCH₃ | CH₃ |
| BB | 7-OH | H | H | H | CH₃ |
| EE | 7-OCH₃ | H | H | H | CH₃ |
| FF | 7-OCH₃ | H | H | H | H | and pharmaceutically acceptable salts thereof.

Also exemplary of compounds of the invention of formula I are:

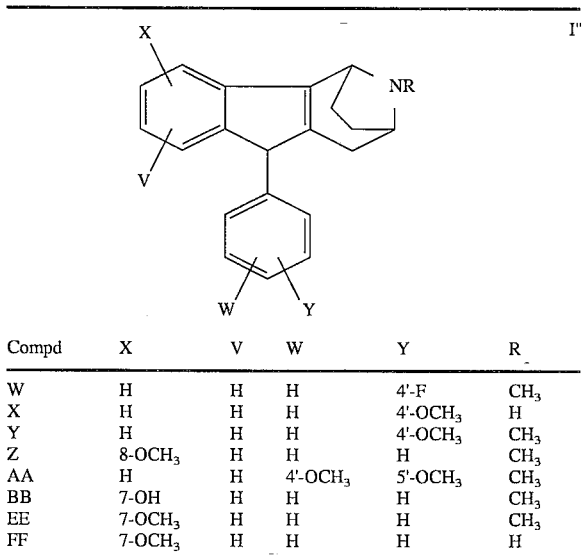

| Compd | X | V | W | Y | R |
|---|---|---|---|---|---|
| W | H | H | H | 4'-F | CH₃ |
| X | H | H | H | 4'-OCH₃ | H |
| Y | H | H | H | 4'-OCH₃ | CH₃ |
| Z | 8-OCH₃ | H | H | H | CH₃ |
| AA | H | H | 4'-OCH₃ | 5'-OCH₃ | CH₃ |
| BB | 7-OH | H | H | H | CH₃ |
| EE | 7-OCH₃ | H | H | H | CH₃ |
| FF | 7-OCH₃ | H | H | H | H | and pharmaceutically acceptable salts thereof.

Also exemplary of compounds of the invention of formula I are:

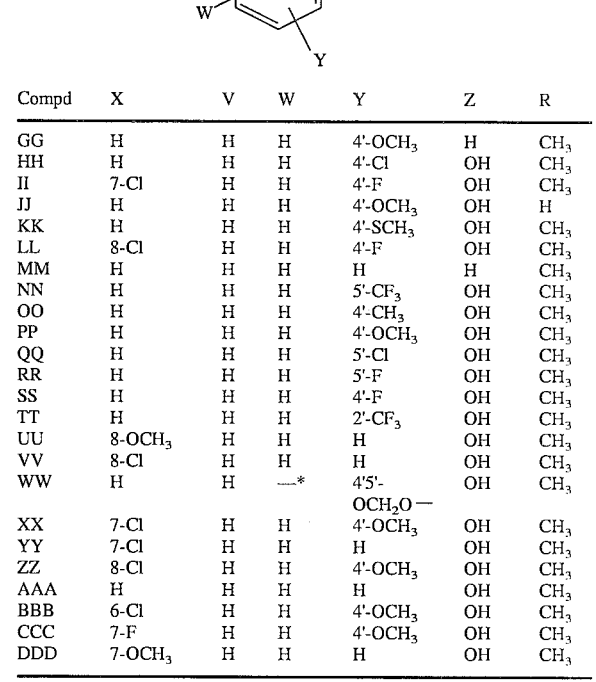

| Compd | X | V | W | Y | Z | R |
|---|---|---|---|---|---|---|
| GG | H | H | H | 4'-OCH₃ | H | CH₃ |
| HH | H | H | H | 4'-Cl | OH | CH₃ |
| II | 7-Cl | H | H | 4'-F | OH | CH₃ |
| JJ | H | H | H | 4'-OCH₃ | OH | H |
| KK | H | H | H | 4'-SCH₃ | OH | CH₃ |
| LL | 8-Cl | H | H | 4'-F | OH | CH₃ |
| MM | H | H | H | H | H | CH₃ |
| NN | H | H | H | 5'-CF₃ | OH | CH₃ |
| OO | H | H | H | 4'-CH₃ | OH | CH₃ |
| PP | H | H | H | 4'-OCH₃ | OH | CH₃ |
| QQ | H | H | H | 5'-Cl | OH | CH₃ |
| RR | H | H | H | 5'-F | OH | CH₃ |
| SS | H | H | H | 4'-F | OH | CH₃ |
| TT | H | H | H | 2'-CF₃ | OH | CH₃ |
| UU | 8-OCH₃ | H | H | H | OH | CH₃ |
| VV | 8-Cl | H | H | H | OH | CH₃ |
| WW | H | H | —* | 4'5'-OCH₂O— | OH | CH₃ |
| XX | 7-Cl | H | H | 4'-OCH₃ | OH | CH₃ |
| YY | 7-Cl | H | H | H | OH | CH₃ |
| ZZ | 8-Cl | H | H | 4'-OCH₃ | OH | CH₃ |
| AAA | H | H | H | H | OH | CH₃ |
| BBB | 6-Cl | H | H | 4'-OCH₃ | OH | CH₃ |
| CCC | 7-F | H | H | 4'-OCH₃ | OH | CH₃ |
| DDD | 7-OCH₃ | H | H | H | OH | CH₃ |

*In the case of compound WW, W and Y together are 4'5'-OCH₂O—.

and pharmaceutically acceptable salts thereof.

Another compound of the invention is

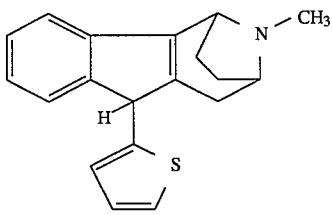
GGG and pharmaceutically acceptable salts thereof.
Another compound of the invention is

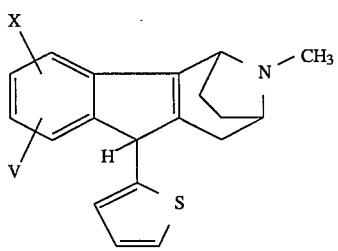
GGG and pharmaceutically acceptable salts thereof.
The most preferred compound of the invention is

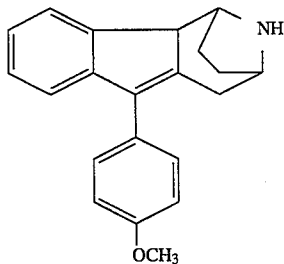

This compound will at times be referred to in the specification as compound B.

The compounds of formulas I are useful as agents in the treatment of allergies and bronchoconstriction. The present invention also provides pharmaceutical compositions for treating patients afflicted with allergies and bronchoconstriction which comprises an anti-allergy effective amount of a compound of formulas I and a pharmaceutically acceptable carrier therefor. The present invention also provides methods of treating a patient afflicted with allergies or bronchoconstriction which comprises administering to said patient an anti-allergy or anti-bronchoconstriction effective amount of a compound of formulas I.

The compounds of formulas I are useful as agents in the treatment of CNS diseases and conditions such as depression, psychoses, and drug dependence. The present invention also provides pharmaceutical compositions for treating patients afflicted with CNS diseases and conditions such as depression, psychoses, and drug dependence which comprises an anti-depression, anti-psychoses, or anti-drug dependence effective amounts of a compound of formulas I or IX and a pharmaceutically acceptable carrier therefor. The present invention also provides methods of treating a patient afflicted with CNS diseases and conditions, which comprises administering to said patient an anti-depression, anti-psychoses, or anti-drug dependence disease effective amount of a compound of formulas I.

Also preferred are compounds of formula I with the proviso that when Z is OH, b and a are not bonds, and at least one of X and V are halogen, then neither W nor Y can be O—($C_1$–$C_8$)alkyl, in the 4'-position. The just above mentioned compounds, as well as compound GGG, are inhibitors of i) cell adhesion to extracellular matrix proteins such as fibronectin and vitronectin, ii) invasion of tumor cells through extracellular matrix, and iii) tumor metastasis. Therefore, these just above mentioned compounds and compound GGG are useful as agents in the treatment of tumors, in humans, in general, as well as agents in inhibiting tumor metastasis, in humans, in particular. The present invention also provides pharmaceutical compositions for treating patients afflicted with tumors which comprises an anti-tumor effective amount of one of the just above mentioned compounds of formula I and a pharmaceutically acceptable carrier therefor. The present invention also provides methods of treating a patient afflicted with tumors which comprises administering to said patient an anti-tumor effective amount of one of the just above mentioned compounds of formula I.

DETAILED DESCRIPTION OF THE INVENTION

As used herein, the term "alkyl" refers to straight and branched chain hydrocarbon groups of 1 to 20 carbon atoms, such as methyl, ethyl, n-, and iso-propyl, n-, sec- and tert-butyl, n-, sec-, iso-, tert- and neo-pentyl, n-, sec-, iso-, tert-hexyl and n-, sec-, iso-, tert-, and neo-heptyl and n-, sec-, iso-, tert-, and neo-octyl. Alternatively, the number of carbon atoms in a particular alkyl may be designated. For example, "($C_1$–$C_8$)alkyl" refers to an alkyl as decribed above, having 1 to 8 carbon atoms. The preferred alkyl is methyl.

As used herein, the term "alkenyl" refers to straight and branched alkenyl groups of 2 to 20 carbon atoms, such as —CH=$CH_2$, —CH=CH$CH_3$, and —CH=C(C$H_3$)C$H_3$. Alternatively, the number of carbon atoms in a particular alkenyl may be designated. For example, "($C_3$–$C_8$)alkenyl" refers to an alkenyl as decribed above, having 3 to 8 carbon atoms.

As used herein, the term "alkynyl" refers to straight and branched alkynyl groups of 2 to 20 carbon atoms, such as —C≡CH, —C≡CC$H_3$, —C≡—C$H_2$C$H_3$ and —C≡C—CH(C$H_3$)C$H_3$. Alternatively, the number of carbon atoms in a particular alkynyl may be designated. For example, "($C_3$–$C_8$)alkynyl" refers to an alkynyl as decribed above, having 3 to 8 carbon atoms.

As used herein, the term "cycloalkyl" refers to cycloalkyl groups of 3 to 10 carbon atoms, such as cyclopropyl ,cyclobutyl and cyclopentyl Alternatively, the number of carbon atoms in a particular cycloalkyl may be designated. For example, "($C_3$–$C_8$)cycloalkyl" refers to an cycloalkyl as decribed above, having 3 to 8 carbon atoms.

As used herein, the term "halogen" refers to chlorine, bromine iodine, and fluorine.

The positions on the rings of the compounds of the invention are numbered in formula XXX just below as follows:

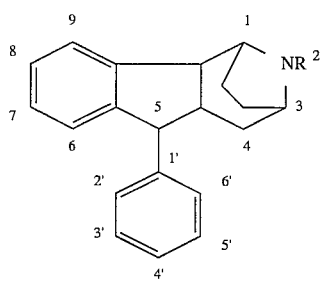

The term "pharmaceutically acceptable salt" refers to salts with the following acids: hydrobromic, hydrochloric, sulfuric, phosphoric, acetic, citric, oxalic, malonic, salicylic, malic, fumaric, succinic, tartaric, ascorbic, maleic, methanesulfonic, propionic, valeric, oleic, palmitic, stearic, lauric, benzoic, lactic, para-toluenesulfonic, fumaric, and the like, and other mineral and carboxylic acids well known to those skilled in the art. One skilled in the art will realize that acid addition salts of the compounds of the invention may be made with such salts whenever a basic functionality is present in a particular compound of the invention.

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

The compounds of formula I of the invention may be prepared as shown below.

REACTION SCHEME 1

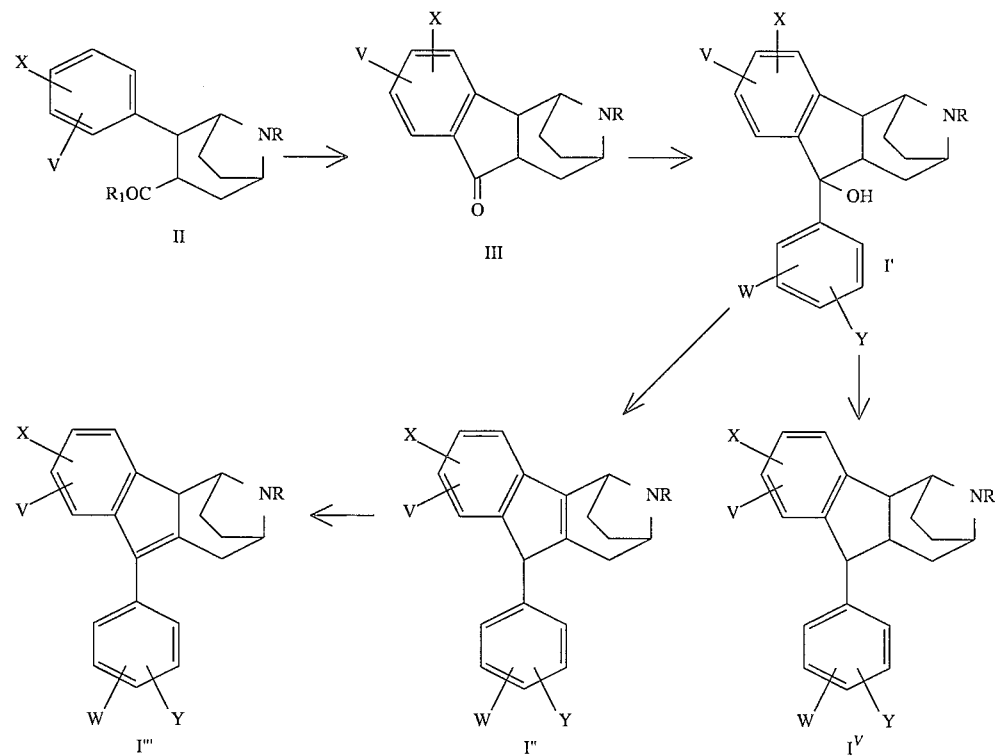

wherein X, V, W, Y and R are as described above; and $R_1$ is —OH, Cl, or Br unless otherwise noted.

In the above reaction scheme, a compound of formula II may be reacted with a strong acid, which may be either a protic acid or a Lewis acid. For example, Eaton's reagent ($P_2O_5$:$MeSO_3H$(1:10)), $AlCl_3$, polyphosphoric acid (PPA), zinc chloride, or titanium tetrachloride may be used. The most preferred Lewis acid is $AlCl_3$. The reaction is carried out in a suitable solvent such as a chlorinated hydrocarbon like methylene chloride, chloroform, or more preferably tetrachloroethane. On conventional work-up, a compound of formula III may be obtained.

For example, a compound of formula II wherein $R_1$ is —OH or Cl may be dissolved in about 5 to about 100, most preferably 50 times its weight of a cyclo-dehydrating reagent, such as PPA, or more preferably Eaton's Reagent ($P_2O_5$:$MeSO_3H$(1:10)) stirred and gradually heated to a temperature in the range of about 60° to about 150° C., most preferably about 90°–110° C. for about 6 to about 20 hours, most preferably about 8 hours. The resulting product may be worked up by conventional means to obtain a compound of formula III.

Alternatively, a compound of formula II wherein $R_1$ is —OH or Cl may be dissolved in $(CHCl_2)_2$, and treated with a Lewis acid such as $AlCl_3$ at a temperature in the range of about 40° C. to about 60° C. more preferably 45° C. The resulting product may be worked up by conventional means to obtain a compound of formula III. A reaction of this type is described in Example 5 below and one skilled in the art would be able to run reactions analogous to that of Example 5 below.

A compound of formula III is reacted with a Grignard reagent of the formula:

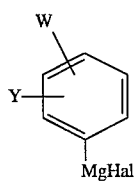

wherein W and Y are as described herein, and Hal is Br, Cl or I;
or an aryl lithium reagent of the formula:

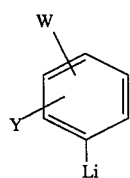

wherein W and Y are as described herein.

When a Grignard reagent is used, the reaction is run in an aprotic, organic solvent such as dioxane, diethyl ether, 1,2-dimethoxyethane (glyme), tetrahydrofuran or tetrahydrofuran with methylene chloride as a co-solvent at a temperature in the range of about −80° C. to about 0° C., preferably at about −50° C., for about 1 to about 8 hours most preferably about 3 hours to obtain a compound of formula I'.

Exemplary of Grignard reagents which may be employed are 4-chloro-phenyl magnesium bromide, 3-trifluoromethyl-4-chlorophenyl magnesium bromide, 3-methylmercaptophenyl-magnesium bromide, phenyl magnesium bromide, or 4-methoxyphenyl magnesium bromide.

When an aryl lithium reagent is used, the reaction is run in an ether solvent such as diethyl ether, tetrahydrofuran (THF), or glyme, (1,2-bis-methoxyethane) at a temperature at or below room temperature such as (−25° C.)–(−40° C.) and worked up in a conventional manner to yield carbinols of the invention of formula I'. Exemplary of aryl lithium reagents are phenyl lithium, 4-chloro-phenyl lithium, 3-chloro-phenyl lithium, or 4-methoxy-phenyl lithium.

Grignard reagents and aryl lithium reagents shown above are known or can be prepared in accordance with known methods.

A compound of the formula I', is treated with a dehydrating reagent, such as a strong mineral acid like sulfuric acid, or more preferably hydrochloric acid in a polar protic organic solvent such as methanol or ethanol, at a temperature in the range of about room temperature to reflux temperature of the reaction mixture preferably reflux, (usually the range will be about 50°–125° C.), under an inert atmosphere such as argon or nitrogen, for about 2 to about 4 hours, most preferably about two and one quarter hours, to obtain, after conventional workup, compounds of the formula I".

A compound of the formula I", is treated with a strong organic base, such as tetra-n-butyl ammonium hydroxide, n-benzyltriethylammonium hydroxide or more preferably n-benzyltrimethylammonium hydroxide which is Triton B, in a polar, protic organic solvent such as a lower alcohol, like butanol, propanol, ethanol, or more preferably methanol, at a temperature in the range of about 0° C. to about 50° C., more preferably at about room temperature for a period of about 1 to about 24 hours, to obtain, after conventional workup, a compound of the formula I'''.

A compound of the formula I', may also be treated with a reducing agent, such as $NaBH_4$, in trifluoroacetic acid to obtain, after conventional workup, a compound of the formula $I^{IV}$ as shown in examples 6 and 8 below.

Formula $I^{IV}$ encompasses the compounds of the formula I' and the compounds of the formula $I^V$.

The compounds of formula II are disclosed in U.S. Pat. No. 4,179,567 issued Dec. 18, 1979, which is hereby incorporated by reference, or else they can be prepared by methods analogous to those set forth in U.S. Pat. No. 4,179,567.

Suitable derivatives of compounds of formula II in Reaction Scheme 1 above, may be employed to prepare compounds of the invention. For example, an ester of a compound of formula II is shown as the starting material in the reactions given in example 5 below. Esters of compounds of formula II may be prepared as disclosed in U.S. Pat. No. 4,179,567 mentioned above.

Compounds of formula IX as described in the present specification may also be prepared by methods which are analogous to those set forth for the preparation of compounds of formula I.

Bronchodilating, antidepressant activities and anti-tumor properties of the compounds of the invention can be demonstrated by the following test procedures:

Biological Activity of the Compounds of the Invention

Bronchodilator (in vivo) Guinea Pig Dyspnea

Unanesthetized guinea pigs (250–350 g), fasted overnight were placed in individual closed aerosol chambers which were connected to a Monoghan Ultrasonic nebulizer. The nebulizer can deliver an ultrasonic fog of uniform particles in a range of 1–8 microns. A 0.1% solution of histamine is aerosolized into the chambers causing the guinea pigs to develop dyspnea. The test drug was given orally one hour before the histamine challenge and the onset of dyspnea was recorded. Saline control animals developed dyspnea within 90–120 seconds of aerosol exposure. If a guinea pig showed no signs of dyspnea for 600 seconds of histamine exposure it was considered a survivor. The data was expressed as the number tested over the number survived. The model was sensitive to bronchodilator and H1 antihistamine activity. Further information relating this test can be obtained from the following two publications which are hereby incorporated by reference: Dungan, K. W. and Lish, P. M. J Allergy 32:139–151 (1961). and Lish, P. M., Robbins, S. I. and Petres E. L. J. Pharmacol. Exp. Therap. 153 L 1538 (1966).

Pulmonary Resistance in the Anesthetized Rat

Rats (400–500 g) anesthetized with dialurethane were surgically prepared with tracheal and esophageal catheters. These catheters were connected to pressure transducers for recording of air flow, tracheal and esophageal pressures. These pressures formed the basis for measurement of pulmonary resistance. Inhibition of pulmonary resistance is a reflection of bronchodilation.

All compounds were tested i. v. in 5 separate animals. All data are expressed in % decrease in the pre-drug baseline resistance and each number given is the mean of the 5 animals tested.

The model is sensitive to bronchodilator activity.

Further information relating this test can be obtained from the following publications which are hereby incorporated by reference: Comroe et al, J. Appl. Physio. 4:439–44 (1959); Dungan et al J. Pharmacol. Exp. Therap. 164:290–301(1968); and Mead, J. et al. J. Appl. Physio. 5:779–796 (1953).

Data from compounds of the invention in the following tests are as follows:

TABLE 1

| CMPD | DYSP Dose (mg/kg) | Survivors | Pulmonary Resistance in Rats at a dose of 0.5 mpk, % Inhibition |
|---|---|---|---|
| A | 100 | 2/3 | |
| B | 100 | 0/3 | |
| C | 100 | 0/3 | |
| D | 100 | 1/3 | |
| E | 100 | 0/3 | |
| F | 100 | 0/3 | |
| G | 100 | 1/3 | |
| H | 100 | 1/3 | 20 |
| W | 100 | 2/3 | 21 |
| | 50 | 2/3 | |
| | 20 | 2/3 | |
| | 10 | 1/3 | |
| I | 100 | 1/3 | |
| J | 100 | 2/3 | 35 |
| | 50 | 1/3 | |
| | 10 | 0/3 | |
| K | 100 | 2/3 | 34 |
| | 60 | 1/3 | |
| | 30 | 0/3 | |
| L | 100 | 2/3 | 14 |
| W | 100 | 0/3 | |
| M | 100 | 0/3 | |
| O | 100 | 0/3 | |
| P | 50 | 0/3 | 12 |
| Y | | 2/3 | |
| Q | 100 | 0/3 | 24 |
| R | 100 | 1/3 | 26 |
| S | 100 | 0/3 | |
| T | 100 | 2/3 | 46 |
| | 50 | 0/3 | |
| Z | 100 | 0/3 | |
| GG | 100 | 2/3 | |
| HH | 100 | 1/3 | |
| II | 100 | 3/3 | |
| JJ | 100 | 2/3 | |
| | 50 | 1/3 | |
| KK | 50 | 0/3 | |
| MM | 100 | 2/3 | 9 |
| | 50 | 0/3 | |
| NN | 50 | 0/3 | |
| OO | 100 | 1/3 | −18 |
| AA | 100 | 0/3 | 6 |
| PP | 50 | 0/3 | 62 |
| QQ | 50 | 1/3 | −30 |
| RR | 100 | 2/3 | 28 |
| | 50 | 0/3 | |
| SS | 100 | 3/3 | 22 |
| | 50 | 1/3 | |
| TT | 50 | 0/3 | 7 |
| UU | | | 2 |
| VV | 100 | 3/3 | |
| WW | | | 39 |
| XX | 100 | 3/3 | |
| | 50 | 3/3 | |
| | 20 | 2/3 | |
| | 10 | 2/3 | |
| YY | 100 | 2/3 | |
| | 50 | 3/3 | |
| ZZ | 100 | 1/3 | |
| AAA | 50 | 0/3 | 35 |
| BBB | 100 | 1/3 | |
| CCC | 100 | 2/3 | |
| N | 100 | 0/3 | 33 |
| FF | 100 | 0/3 | 2 |
| V | 100 | 0/3 | |

As used herein, CMPD refers to compound;

DYSP refers to the Bronchodilator (in vivo) Guinea Pig Dyspnea test at 100 mpk and at other dosages shown in the table above.

The above data indicate that the compounds of formula I are active as agents in the treatment of allergies.

Acetic Acid Writhing Test in Mice

The blockade of writhing induced by the intraperitoneal injection of acetic acid is an established experimental animal model for the screening of antinociceptive drugs (drugs which prevent the appreciation or transmission of pain sensations).

The procedure for the Acetic Acid Writhing Test in Mice is set forth in Hendershot et al, *J. Pharmacol. Exp. Therap.* 125:237, (1959); Koster et al., *Fed. Proc.* 18:412, (1959); and international application PCT/US91/06705, filed 20 Sep. 1991, which are hereby incorporated by reference.

The results for this test are given below in the units of mg/kg which is also abbreviated in this specification as mpk. The results for this test are given as effective doses ($ED_{50}$'s).

EFFECTS ON TETRABENAZINE (TBZ)-INDUCED PTOSIS IN MICE

Clinically active antidepressant drugs are known to block TBZ-induced ptosis in mice (See Psychosomatic Medicine, Nodine and Moyer, Eds. Lea and Febiger, Philadelphia, 1962, pp 683–90, which is hereby incorporated by reference). Activity in this test is used to predict anti-depressant activity in man.

The procedure for the TBZ-Induced Ptosis Test in Mice is set forth in Psychosomatic Medicine, Nodine and Moyer, Eds. Lea and Febiger, which is hereby incorporated by reference and in PCT/US91/06705, filed 20 Sep. 1991, which is mentioned above.

The results for this test are given below as $ED_{50}$'s in the units of mg/kg.

EFFECTS ON MURICIDAL BEHAVIOR IN RATS

Blockade of muricidal (mouse-killing) behavior in rats is used as a measure of evaluating the anti-depressant activity of drugs, and the procedure for carrying out this test is set forth in Int. J. Neuro-pharmacal., 5, 405–411 (1966) are hereby incorporated by reference, and in PCT/US91/06705, filed 20 Sep. 1991, which is mentioned above.

The results for this test are given below as $ED_{50}$'s in the units of mg/kg.

CONDITIONED AVOIDANCE SUPPRESSION IN RATS

Clinically active antipyschotic drugs are known to depress discrete trial avoidance behavior in doses that do not retard escape response. See Ann. N.Y. Acad. Sci. 66,740 (1957) which is hereby incorporated by reference. The procedure for carrying out this test is set forth in Int. J. Neuropharmacal., 5, 405–411 (1966) which is hereby incorporated by reference and in PCT/US91/06705, filed 20 Sep. 1991, which is mentioned above.

The results for this test are given below as minimum effecive doses (MED)in the units of mg/kg.

METHAMPHETAMINE TOXICITY TEST IN MICE

The methamphetamine toxicity test in mice was carried out as described in Burn et al, Arch. Int. Pharmacodyn 113:290–295, (1958); and Coscia et al, Arzneim-Forsch (Drug Research) 25:1436–1442, (1975); which are hereby incorporated by reference.

The results for this test are given below as ED50's in the units of mg/kg.

ANTI-METRAZOLE TEST IN MICE

The anti-metrazole test in mice was carried out as described in Everett et al, J. Pharmacol. Exp. Therap. 81:402–407 (1944); which is hereby incorporated by reference.

The results for this test are given below as ED50's in the units of mg/kg.
Data from compounds of the invention in the following tests are as follows:

TABLE 2

| CMPD | CAR | MUR | TBZ | METHA | MTZ | WRITH |
|---|---|---|---|---|---|---|
| T | >25 | >10 | 5.7 | | >30 | 17.3 |
| Q | | >10 | 3.6 | | >30 | >30 |
| R | | | 17.3 | >30 | >30 | >30 |
| B | | | 12.0 | >30 | >30 | >30 |
| V | | | >30 | | | |
| K | | | >30c | 14.9 | >30 | |
| U | >25 | 14.1 | 1.3 | | >30 | >30 |
| Y | | >20 | 0.35 | >30 | | |
| X | | >30 | 17.3 | >60 | | >30 |
| EE | >25 | | >30 | | >30 | >30 |
| FF | | | >30 | >30 | >30 | >30 |
| Z | | | >30 | >30 | >30 | 17.3 |
| AA | | >10 | >30 | >30 | >30 | 22.8 |
| W | | | >30 | 8.9 | >30 | 10.7 |
| AAA | | >10 | >30 | >30 | >30 | >30 |
| PP | >25 | >10 | >30 | | >30 | >30 |
| JJ | | | >30 | >30 | >30 | >30 |
| DDD | >25 | 3.8 | >30 | | >30 | >30 |
| UU | | | >30 | >30 | >30 | 17.3 |
| SS | | >10 | >30 | >30 | >30 | >30 |
| MM | | >10 | 9.3 | | | |

As used herein, CAR refers to the conditioned avoidance suppression test in rats;
MUR refers to the test on the effects on muricidal behavior in rats;
TBZ refers to the test of effects on tetrabenazine induced ptosis in mice, p.o.;
METHA refers to the methamphetamine toxicity test in mice;
WRITH refers to the acetic acid writhing test in mice, p.o.
c animals were ataxic and depressed at this dose.

The above data indicate that the compounds of formula I are active as agents in the treatment of CNS diseases and conditions such as depression, psychoses, and drug dependence.

Synthetic peptides containing the RGD sequence (arginine-glycine-aspartate) derived from the fibronectin sequence block metastasis of melanoma cells in vivo (Humphries et al. (1988) J. Clin. Invest. 81:782). These RGD peptides are known to act by competitive blockade of cell adhesion to extracellular matrix glycoproteins such as fibronectin. The compounds of the invention also inhibit tumor cell adhesion to fibronectin and other extracellular matrix glycoproteins and therefore are believed to inhibit tumor metastasis.

Metastasis, the major cause of cancer deaths, is the process by which tumor cells break away from a primary tumor, migrate to distal sites, and form secondary tumors. Once tumor cells leave a primary tumor and are released into the circulation, they must attach to the subendothelial extracellular matrix before they can invade the neighboring tissue. Fibronectin is an important extracellular matrix glycoprotein to which tumor cells adhere.

The present specification details the ability of compound B and other compounds of the invention to block i) melanoma cell adhesion to fibronectin and other extracellular matrix glycoproteins in vitro, ii) melanoma cell invasion through a fibronectin/collagen matrix in vitro, and iii) experimental metastasis of melanoma cells to the lung in vivo.

Data are also included to address the selectivity of the compounds for blockade of fibronectin adhesion relative to i) cytotoxic effects and ii) blockade of cell adhesion to cell-surface adhesion receptors, such as ICAM-1 and ELAM-1.

Cell Adhesion and other Assay Procedures

Adhesion Assays

Adhesion assays were run essentially as described previously (Pai et al., J. Biomed. Res. 2: 53, 1992). 96-well plates were coated with human fibronectin (140 ng/well), human vitronectin (75 ng/well), human collagen I (100 ng/well), human collagen IV (100 ng/well), human fibrinogen (1 µg/well), murine laminin (600 ng/well), or polylysine, and incubated overnight in a humidified 37° C. incubator. Excess fibronectin or other substrate was then removed and 0.2 ml of 2 mg/ml bovine serum albumin (BSA)in Dulbecco's phosphate-buffered saline (DPBS) was added to each well, incubated for 2 hours at 37° C., and removed. LOX human melanoma cells, M27 murine lung carcinoma cells or B16F10 mouse melanoma cells were detached from tissue culture flasks with RPMI medium containing 0.2M urea and 10 mM EDTA, and 0.18 ml of cells were added to each well to a final cell concentration of $1 \times 10^5$ cells/well. For inhibition studies 20 µl of 10× compound was added to the wells prior to cell addition. Cells were allowed to adhere for 1 hour at 37° C. The wells were then gently washed twice with 0.2 ml DPBS. The fluorescent dye calcein AM (Molecular Probes, Eugene Oreg.) in DPBS (0.1 ml of 1 µM) was added to each well, and the plates were incubated for 1 hour at room temperature. Adherent cells were quantitated by reading the fluorescence on a Cytofluor 2300 fluorescent plate reader (Millipore) at 485 nm excitation and 530 nm emission.

For measurement of cell adhesion to ICAM-1, HL-60 human leukemia cells were induced to differentiate in the presence of DMSO for 6 days. Adhesion of DMSO-differentiated HL-60 cells to recombinant soluble ICAM-1 (2 µg/well) was measured as described above for LOX cell adhesion, except that the adhesion was allowed to proceed for 30 minutes, rather than 1 hour, at 37° C.

Cell adhesion to ELAM-1 was measured essentially as described previously (Pal et al., J. Biomed. Res. 2: 53, 1992). Undifferentiated HL-60 leukemia cells were prelabelled for 30 minutes with 1 µM calcein AM in DPBS without calcium or magnesium, and the cells were washed twice with the same medium before addition to 96-well plates containing monolayers of mouse L cells ($5 \times 10^4$ cells/well) transfected with cDNA for the adhesion molecule ELAM-1. Adhesion was allowed to proceed for 30 minutes at room temperature before washing and quantitation of the remaining fluorescent HL-60 cells as described above.

Calcein Cytotoxicity Assay

LOX human melanoma cells were detached from tissue culture flasks with RPMI medium containing 0.2M urea and 10 mM EDTA, and 0.18 ml of cells were added to each well to a final cell concentration of $5 \times 10^4$ cells/well. 20 µl of 10× compound was added to the wells prior to cell addition. Cells were incubated with the compound at 37° C. for 1 hour or 5 hour as indicated. Calcein AM in DPBS (0.02 ml of 5 µM) was added to each well, and the plates were incubated for an additional 1 hour at room temperature. Viable cells were quantitated by reading the fluorescence on a Cytofluor 2300 fluorescent plate reader at 485 nm excitation and 530 nm emission.

MTT Cytotoxicity Assay

LOX human melanoma cells, in RPMI medium with 2 mg/ml BSA and 25 mM HEPES, pH 7.4, were seeded at $4 \times 10^4$ cells/well in 96-well microtiter plates and grown overnight in a humidified 37° C. incubator. On the following day, the medium was aspirated and wells were washed once with 0.1 ml of DPBS. Compounds (0.1 ml) in DPBS were added to wells in quadruplicate at appropriate concentrations. The cells were then incubated with test compound for 1 hour at 37° C. Wells were aspirated and washed 2× with 0.1 ml DPBS. MTT [3-( 4,5-Dimethylthiazol-2-yl)-2,5-diphenyltetrazolium bromide] (0.1 ml of 1 mg/ml solution in PBS from Sigma Chemical Co.) was added to each well and incubated for 2 hour at 37° C. MTT was aspirated and 0.1 ml of 50% N,N-dimethylformamide with 20% sodium dodecyl sulfate was added to each well. Plates were shaken for 10 minutes on a Titer-Plate shaker (Labline) at room temperature. Optical density was read at 570 nm with a plate-reading spectrophotometer (Dynatech MR5000).

Tremor Cell Invasion Through Collagen/Fibronectin Coated Membranes:

Nucleopore polycarbonate membranes (8 µm pore size) were coated with 0.05 ml of type I collagen and allowed to dry overnight. 210 µl of serum free DMEM with BSA was added to each Boyden chamber. Membranes were placed in chambers and upper chambers were screwed on. Human fibronectin (50 µl of 0.1 mg/ml solution in DMEM with BSA) was added to the top chamber and allowed to sit on membranes for 1 hour at room temperature. Compounds (50 µl) at 10× concentration in DMEM with BSA were added to the chambers. LOX melanoma cells were detached from flasks with trypsin/EDTA solution and resuspended in RPMI with 10% fetal bovine serum. Cells were centrifuged, washed 2× with DMEM with BSA, and resuspended in 10 ml of DMEM with BSA. LOX cells (0.45 ml of $7.8 \times 10^5$ cells per ml) were added to each chamber and chambers were incubated for 5 hours at 37° C. The medium was removed from the upper chamber by aspiration, the top chamber was unscrewed, and the membrane was removed. The membrane was inverted, pinned to a dissecting tray, and fixed with Diff Quik fixative for 3 minutes The fixative was then removed and Diff Quik Stain was added for 2 minutes. The stain was decanted and membranes were rinsed with distilled water. Membranes were inverted onto glass slides, and non-invading cells were wiped away with a cotton swab. Permount was added to the slide and the membrane was covered with a cover slip. The number of cells that invaded was quantitated on a Nikon TMS microscope with C-2 Image Analyzer software (Olympus Corp.).

Table 3, just below, shows that compounds of formula I of the invention inhibit tumor cell attachment to fibronectin.

TABLE 3

Inhibition of LOX Melanoma Cell Adhesion to Fibronectin
% Inhibition at 10 µM and 50 µM

| Compound | % Inhibition at 10 µM | % Inhibition at 50 µM |
| --- | --- | --- |
| A | 81.1 | 100.8 |
| B | 61.8 | 101.3 |
| C | 58.6 | 100.7 |
| D | 56.5 | 101.0 |
| E | 49.5 | 100.0 |
| F | 49.4 | 101.6 |
| G | 38.1 | 101.3 |
| H | 37.5 | 101.2 |
| W | 36.3 | 100.1 |
| I | 35.6 | 100.0 |
| J | 31.1 | 100.7 |
| K | 27.6 | 100.5 |
| L | 23.7 | 100.5 |
| X | 20.8 | 99.7 |
| M | 18.4 | 99.6 |
| N | 7.0 | 101.2 |

TABLE 3-continued

Inhibition of LOX Melanoma Cell Adhesion to Fibronectin
% Inhibition at 10 μM and 50 μM

| Compound | % Inhibition at 10 μM | % Inhibition at 50 μM |
|---|---|---|
| O | 5.2 | 97.1 |
| P | −2.4 | 99.8 |
| Y | −1.2 | 98.2 |
| Q | 0.1 | 97.1 |
| R | −27.3 | 97.1 |
| S | −4.4 | 90.2 |
| T | 2.2 | 89.3 |
| Z | −27.6 | 67.0 |
| GGG | −27.6 | 64.4 |
| GG | 7.1 | 39.1 |
| HH | 2.5 | 36.9 |
| II | 5.4 | 34.8 |
| JJ | 10.1 | 33.7 |
| KK | 7.2 | 32.8 |
| LL | −12.2 | 26.6 |
| MM | −1.8 | 25.8 |
| NN | 9.4 | 24.7 |
| OO | 6.6 | 23.7 |
| AA | −30.0 | 23.6 |
| PP | 4.9 | 21.9 |
| QQ | 9.2 | 21.1 |
| U | −18.7 | 21.0 |
| RR | 13.8 | 17.6 |
| SS | 10.1 | 17.3 |
| TT | 16.7 | 16.1 |
| UU | 10.3 | 15.9 |
| VV | 0.9 | 15.9 |
| WW | 1.2 | 11.9 |
| XX | −23.1 | 8.1 |
| YY | −14.6 | 7.4 |
| ZZ | −9.7 | 7.0 |
| BB | −38.2 | 6.5 |
| AAA | 5.2 | 5.8 |
| BBB | −11.8 | 5.6 |

After these compounds showed activity in inhibition of tumor cell adhesion to fibronectin, the compounds were tested to determine whether they selectively inhibit LOX melanoma cell adhesion to fibronectin relative to cytotoxicity (See 2 Hr Tox, MTT 1Hr, and 6Hr Tox in Table 4). Several of the compounds were also tested for inhibition of adhesion of other tumor cell types (M27 and B16) to fibronectin. The data in Table 4 below demonstrate that the compounds of the invention are selective inhibitors of adhesion of multiple tumor cell types to fibronectin relative to cytotoxicity. In addition, compounds B, C, F and J have been shown to inhibit in vitro tumor cell invasion through a fibronectin/collagen matrix. This anti-invasive activity is a further indication that the compounds of the invention have anti-metastatic activity.

All $IC_{50}$ and $LD_{50}$ values given below are in μM.

TABLE 4

Effects of Compound B and other compounds of the invention on Tumor Cell Adhesion, Invasion and Cytotoxicity

| Cmpd | LOX FN | 2 Hr Tox | MTT 1 Hr | M27 FN | B16 FN | Invasion | 6 Hr Tox | Poly Lys | ELAM-1 | ICAM-1 |
|---|---|---|---|---|---|---|---|---|---|---|
| A | 4.8 | 17.4 | | | | | 5.9 | 11.8 | 21.8 | |
| B | 5.1 | 74.5 | 97.6 | 17.1 | 14.7 | <0.40 | 24.6 | 22.3 | >50 | >50 |
| F | 5.1 | 43.3 | 51.7 | 8.7 | 24.2 | .52 | 19.9 | 24.4 | >50 | 16.8 |
| G | 5.3 | 29.5 | | | | | | 63 | | |
| J | 5.3 | 58.4 | 54.6 | 17.9 | 15.9 | .48 | 30.6 | 53.2 | >50 | >50 |
| E | 6.2 | 21.8 | | | | | | 46.2 | | |
| H | 6.5 | 36.9 | | | | | | 23.7 | | |
| C | 7.3 | 85.3 | 95.1 | 13.7 | 15.1 | .66 | 22.5 | 247.8 | >50 | 24.8 |
| D | 7.4 | 34.6 | | | | | | 71.9 | | |
| I | 7.6 | 55.9 | | | | | | 22.8 | | |
| O | 11.2 | 72 | | | | | | 130.3 | | |
| P | 11.7 | 64.3 | | | | | | 296.6 | | |
| M | 12.5 | 39.8 | | | | | | 72.7 | | |
| R | 15 | 137.8 | | | | | | 111.7 | | |
| X | 15 | 67.7 | | | | | | 121 | | |
| K | 15.5 | 116.3 | | | | | | 71.6 | | |
| W | 17.4 | 102.7 | | | | | | 78.3 | | |
| S | 17.7 | >250 | | | | | | >250 | | |
| Q | 19.1 | 66.7 | | | | | | 83.6 | | |
| N | 19.4 | 23.8 | | | | | | 25.3 | | |
| T | 19.5 | 134.9 | | | | | | 114.7 | | |
| L | 20 | 29.7 | | | | | | 80.4 | | |
| Y | 21.6 | 63.6 | | | | | | 105 | | |
| Z | 28.1 | >250 | | | | | | >250 | | |
| SS | >50 | >250 | | | | | | >250 | | |

The following is brief description of the tests listed in Table 4 and the reasons why they are included. In describing the tests, compound B will be used as an example.

LOX FN-$IC_{50}$ value for inhibition of adhesion of LOX human melanoma cells to fibronectin coated on a plastic surface.

2 Hour Tox-$LD_{50}$ value for cytotoxicity of compounds to LOX melanoma cells over two hours as measured by calcein AM assay: Indicates 15-fold selectivity of compound B, for blockade of fibronectin adhesion vs. cytotoxicity.

MTT 1 hour-$LD_{50}$ value for cytotoxicity of compounds to LOX melanoma cells over one hour as measured by MTT assay: Indicates 19-fold selectivity of compound B for blockade of fibronectin adhesion vs. cytotoxicity.

M27 FN-$IC_{50}$ value for inhibition of adhesion of M27 mouse lung carcinoma cells to fibronectin coated on a plastic surface: Shows that these compounds also block adhesion of murine tumor cells to fibronectin.

B16 FN-$IC_{50}$ value for inhibition of adhesion of B16-F10 mouse melanoma cells to fibronectin coated on a plastic surface: Shows that these compounds also block adhesion of murine tumor cells to fibronectin.

Invasion-$IC_{50}$ value for inhibition of invasion of LOX human melanoma cells through a fibronectin/collagen matrix: The potent activity of the compounds in this assay suggests that these compounds should also block the ability of tumor cells to invade through tissue to reach sites of secondary tumor formation. The greater potency of the compounds in this assay ($IC_{50}$ for compound B<400 nM) may result from the longer duration of this assay (5 hours) relative to the fibronectin adhesion assay (1 hour).

6 Hour Tox-$LD_{50}$ value for cytotoxicity of compounds to LOX melanoma cells over 6 hours as measured by calcein AM assay: This cytotoxicity assay is run as a control for the 5 hour invasion assay and shows >61-fold selectivity of compound B for blockade of invasion vs. cytotoxicity.

PolyLys-$IC_{50}$ value for inhibition of adhesion of LOX human melanoma cells to polylysine coated on a plastic surface: Indicates that the compounds show some selectivity for inhibition of adhesion to fibronectin relative to adhesion to a nonspecific positively charged surface.

ELAM-1-$IC_{50}$ value for inhibition of adhesion of HL-60 human leukemia cells to mouse L cells transfected with cDNA for the adhesion molecule ELAM-1: Indicates that the compounds show selectivity for inhibition of adhesion to fibronectin relative to adhesion to a different class of adhesion molecule. ELAM-1 (E-selectin) is a member of the selectin class of adhesion molecules.

ICAM-1-$IC_{50}$ value for inhibition of adhesion of HL-60 human leukemia cells to recombinant soluble ICAM-1 coated on a plastic surface: Indicates that the compounds show selectivity for inhibition of adhesion to fibronectin relative to adhesion to a different class of adhesion molecule. ICAM-1 is a cell surface adhesion molecule that participates in cell-cell adhesion interactions, rather than cell-matrix adhesion interactions.

Table 5 below entitled "Inhibition of LOX Cell Adhesion to Various Extracellular Matrix Glycoproteins and Fibrinogen" shows $IC_{50}$ values (μM) for inhibition of adhesion to numerous extracellular matrix constituents which were obtained as described above for cell adhesion assays. The finding that the compounds inhibit adhesion to all of these in a similar dose range suggests that the compounds should be very effective in preventing tumor cell interaction with the extracellular matrix in vivo.

TABLE 5

Inhibition Of LOX Cell Adhesion To Various Extracellular Matrix Glycoproteins and Fibrinogen $IC_{50}$ Values (μM)

| Compnd | Fibro-nectin | Laminin | Colla-gen I | Collag-en IV | Vitro-nectin | Fibrino-gen |
|---|---|---|---|---|---|---|
| B | 5.1 | 7.7 | 6.7 | 16.2 | 16.8 | 9.9 |
| J | 5.3 | 2.5 | 4.5 | 10.0 | 12.8 | 13.5 |
| C | 7.3 | 3.5 | 4.0 | 9.9 | 5.9 | 6.2 |
| S | 17.7 | 7.7 | 11.6 | 19.2 | 20.2 | 15.7 |

In Vivo Experimental Metastasis

C57/black6 female mice (6–7 weeks old) were randomized before any treatment into groups of 5 mice per treatment. Compounds of the invention were prepared as a fine suspension in 25% β-cyclodextran and administered i.p. in a volume of 0.2 ml per animal. Two hours after drug (or vehicle) injection, 0.2 ml of DPBS containing $1 \times 10^5$ B-16 F10 murine melanoma cells were injected i.v. into the tail vein. After 14 days, animals were sacrificed and lungs were removed. Metastatic lung colonies were counted by visual inspection.

Table 6 entitled "Inhibition of B16-F10 Melanoma Metastasis by i.p. Pretreatment with compound B" shows that i.p. treatment of mice with compound B (150 mpk) 2 hours before i.v. injection of melanoma inhibited in vivo metastasis by 73% relative to the vehicle control. Cytoxan (250 mpk) was included as a positive control and showed similar effectiveness.

TABLE 6

Inhibition of B16-F10 Melanoma Metastasis In Vivo By Intraperitoneal Pretreatment with compound B.

| Drug Treatment | Pre-treatment Time* | Number of Lung Melanoma Colonies | % Inhibition by compound B |
|---|---|---|---|
| Vehicle Control | 30 min | 79.4 ± 12.9 | 0% |
| 250 mpk Cytoxan | 30 min | 17.6 ± 4.2 | 77.8% |
| 150 mpk compound B | 30 min | 35.2 ± 13.9 | 55.7% |
| 150 mpk compound B | 120 min | 21.8 ± 2.0 | 72.5% |

*Pretreatment Time is the time between i.p. drug injection and i.v. tumor cell injection.

Based on all of the data in the captioned application, including that of Table 6, above, the compounds of formula I, with the proviso that when Z is OH, b and a are not bonds, and at least one of X and V are halogen, then neither W nor Y can be O—($C_1$–$C_8$)alkyl, in the 4'-position, are believed to be active as agents in inhibiting the metastasis of tumors in mice in general, and more specifically in inhibiting B16-F10 melanoma metastasis in C57/black6 female mice.

Mitogenic effects of growth factors on anchorage-dependent cells have been reported to require integrin-mediated cell attachment. Recently it has been shown that integrin-mediated cell attachment stimulates protein tyrosine phosphorylation and $p21^{ras}$ activation that appear to be involved in cell proliferation.

The potent effect of compound B, as shown in Table 7 below, indicates that the claimed compounds have antiproliferative effects in addition to their antimetastatic effects shown above. Therefore, the compounds of formula I are likely to inhibit tumor growth in addition to inhibiting tumor metastasis.

These data also suggest that the claimed compounds have potential utility as agents useful for the treatment of atherosclerosis.

The procedure for the Smooth Muscle Cell Mitogenesis test is given just below. The fibronectin adhesion inhibitor, compound B, was tested for inhibitory effects on PDGF (Platelet Derived Growth Factor) BB-stimulated mitogenesis of bovine smooth muscle cells. Cells were exposed to PDGF with and without compound B in 24- well plates for 16 hours. Compound B inhibited PDGF-stimulated mitogenesis with an $IC_{50}$ value of 0.52 µM. At 10 µM compound B caused cells to detach from the plate. In a separate PDGF receptor binding assay, compound B was shown not to inhibit PDGF binding directly.

TABLE 7

Inhibition of PDGF-Stimulated Mitogenesis of Bovine Smooth Muscle Cells by compound B

| Drug Treatment | $^3$H-Thymidine Incorporation (dpm/1000 ± S.E.M.) | % Inhibition by compound B |
| --- | --- | --- |
| No Treatment | 120.1 ± 23.9 | |
| 1 ng/ml PDGF-BB | 399.3 ± 20.1 | |
| 1 ng/ml PDGF-BB + 0.1 µM compound B | 406.8 ± 30.2 | −2.7 |
| 1 ng/ml PDGF-BB + 0.3 µM compound B | 347.7 ± 9.8 | 18.5 |
| 1 ng/ml PDGF-BB + 1 µM compound B | 156.3 ± 7.2 | 87.1 |
| 1 ng/ml PDGF-BB + 3 µM compound B | 17.0 ± 1.9 | 136.9 |
| 1 ng/ml PDGF-BB + 10 µM compound B | 7.3 ± 5.3 | 140.4 |

The compounds of this invention can be administered in any number of conventional dosage forms, e.g., topical, oral, parenteral, rectal, transdermal, inhalation and the like. Oral or rectal dosage forms include capsules, tablets, pills, powders, cachets, and suppositories. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, perfumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules.

Similarly, cachets are included. Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical dry, liquid, cream and aerosol formulations. Ointment and creams may, for example, be formulated with an aqueous or oily base with the addition-of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or nonaqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit.

Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

The compounds of this invention may be administered by any conventional mode of administration by employing an effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 0.1 to about 100 mg/kg of body weight per day may be administered to provide bronchodilating, anti-allergy, anti-cancer, or CNS activity.

When administered to humans orally for the treatment of bronchoconstriction, allergy, cancer, or CNS diseases and conditions doses of from about 1 to about 60 mg/kg of body weight may be used; and when administered parenterally, e.g., intravenously, dosages of from about 0.25 to about 20 mg/kg body weight may be used.

When administered topically, the amount of compound administered varies widely with the amount of skin being treated, as well as with the concentration of active ingredient applied to the affected area. Preferably, topical compositions contain from about 0.10 to about 10 percent by weight of the active ingredient and are applied as needed according to the judgment of the attending clinician. When administered rectally, the compounds of this invention may be administered in daily doses ranging from about 0.1 mg/kg to abut 100mg/kg of body weight.

For example, when administered to humans orally for the treatment of tumors, a suitable dosage for compound B would be about 10 mg/kg.

The dosage to be administered and the route of administration depends upon the particular compound used, the age and general health of the patient and the severity of the condition. Thus, the dose ultimately decided upon must be left to the judgment of a trained health-care practitioner.

EXAMPLES

EXAMPLE 1

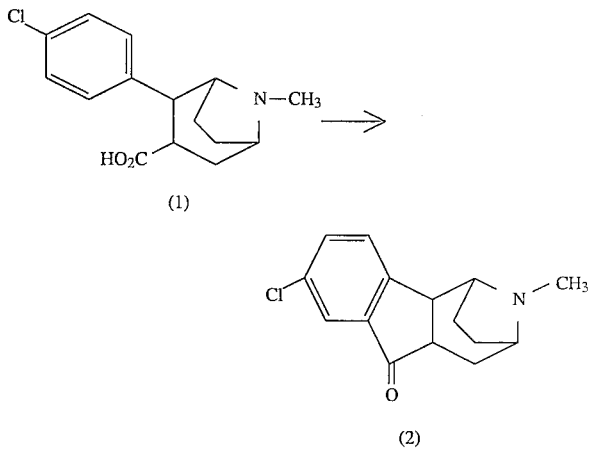

Preparation of 7-Chloro-1,2,3,4,9b,-hexahydro-2-methyl-5H- 1,3-ethanoindeno-(1,2-c)-pyridin-5-one The acid (1) as the hydrochloride salt was dissolved in 50 times its weight of Eaton's Reagent ($P_2O_5$:$MeSO_3H$(1:10)). The reaction mixture was stirred and gradually heated to 90°–110° C. for about 6 to 10 hours.

The reaction mixture was cooled and then poured gradually into water. The reaction mixture was neutralized with $NaHCO_3$(solid). The reaction mixture was basified with concentrated ammonium hydroxide, and extracted with ether. The extracts were dried and evaporated. The product (compound (2)) was crystallized from isopropyl ether to yield a white solid, m.p. 73°–75° C.

Other intermediate compounds prepared in an analogous fashion to the above example were as follows:

| Compound | X | V | m.p. °C. |
|---|---|---|---|
| (i) | H | H | 74–76 |
| (ii) | H | 6-Cl | 112–114 |
| (iii) | H | 8-Cl | 103–105 |

Other intermediate compounds which could be prepared in an analogous fashion to the above example are as follows:

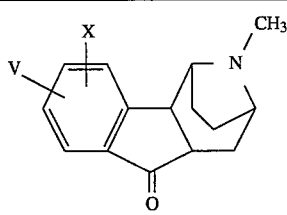

| Compound | X | V |
|---|---|---|
| (iv) | H | 7-F |
| (v) | H | 6-F |
| (vi) | H | 8-F |
| (vii) | H | 7-OCH$_3$ |
| (viii) | H | 8-OCH$_3$ |
| (ix) | H | 7-CF$_3$ |
| (x) | H | 7-SCH$_3$ |
| (xi) | H | 7-SOCH$_3$ |
| (xii) | H | 7-CH$_3$ |
| (xiii) | 7-CH$_3$ | 8-CH$_3$ |
| (xiv) | 8-Cl | 7-OCH$_3$ |
| (xv) | H | 7-CH$_2$CH$_2$OCH$_3$ |
| (xvi) | H | 6-CF$_3$ |
| (xvii) | H | 8-CF$_3$ |
| (xviii) | H | 9-CF$_3$ |
| (xix) | H | 7-NO$_2$ |

EXAMPLE 2

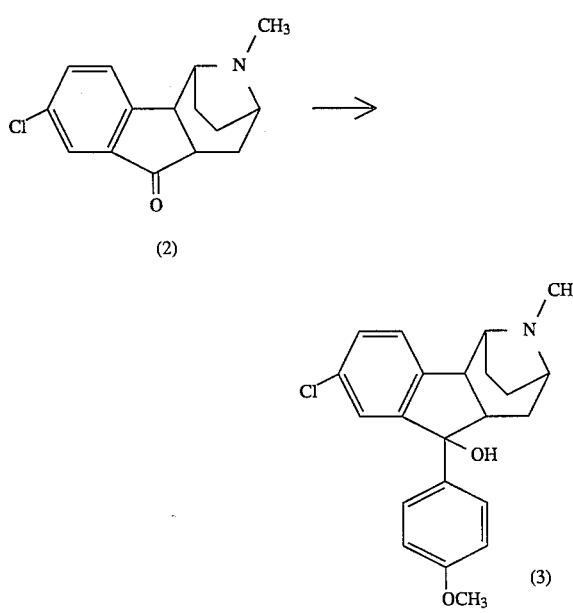

Preparation of 7-Chloro-5-(p-methoxyphenyl)-2-methyl-1,3-ethano-1,2,3,4,4a,9b-hexahydro-5H-indeno[1,2-c]pyridin-5-ol A solution of p-methoxyphenyl magnesium bromide was prepared from p-bromo-anisole (18.5 g) and magnesium (2.5 g)in tetrahydrofuran (50 ml). The solution was cooled to −40° to −50° C. and methylene chloride (25 ml) was added followed by a solution of 7-chloro- 1,2,3,4,4a,9b-hexahydro-2-methyl-5H-1,3-ethanoindeno-[1,2-c]pyridin-5-one (9.16 g) (compound (2))in methylene chloride (40 ml). The solution was stirred first at −50° C. then overnight at 0° C.

The mixture was poured into 20% ammonium chloride solution (125ml). The methylene chloride was separated and washed with 10% sodium hydroxide solution (20 ml), washed with water, dried, concentrated and recrystallized from di-isopropyl ether to yield the compound (3) mp 122°–124° C.

Example 2a

By analogy to the above example 1, other compounds of formula I of the invention were prepared.

EXAMPLE 3

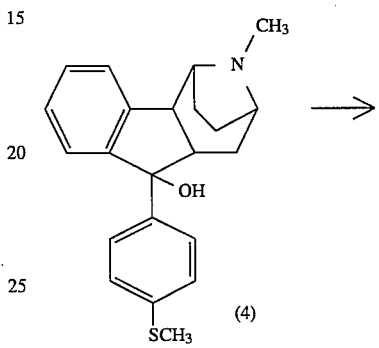

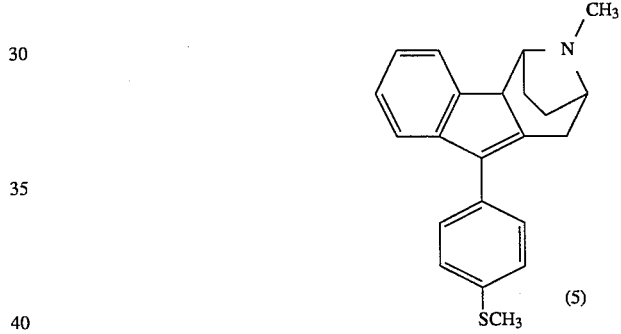

Preparation of 1SR:3RS:9b-1,3 Ethano-2-methy-5-(p-methyl mercaptophenyl)-1,3,4,9b-tetrahydro-2H-indeno-(2h-indeno) [1,2-c]pyridine The compound (4) (6 g) was dissolved in 110 ml of 12% HCl in ethanol at room temperature under an atmosphere of nitrogen. A white precipitate appeared after about 0.5 hour. The mixture was allowed to stand at room temperature overnight, then it was refluxed for 2.25 hours TLC (C$_{18}$ Reversed Phase plates/MeOH) showed that no starting material remained. The product was evaporated to a syrup which was dissolved in water. Concentrated NH3 solution was added resulting in a solid separating out. This was extracted into CH$_2$Cl$_2$ (2X), the organic layer being then separated and evaporated to a gum. This residue was dissolved in methanol to which Triton B was added. The solution was stirred at room temperature overnight. Some white solid had appeared. Water was added, and most of the methanol, was evaporated off. This was repeated. The solid product was filtered off, washed into water and then dried to yield 5.6 g of faintly yellow solid which was compound (5) and which had a m.p. 116°–118° C. (Compound (5) has also been designated as compound F of the invention.)

Analysis Found C:79.28; H 6.97; N, 4.25; S, 9.87 For C$_{22}$H$_{23}$NS Calcd C:79.23; H 6.95; N, 4.20; S, 9.61

EXAMPLE 4.

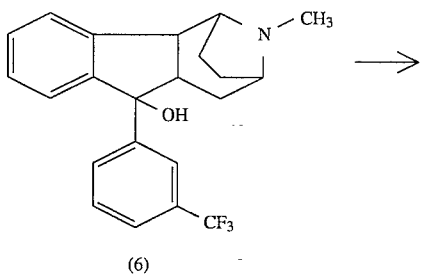

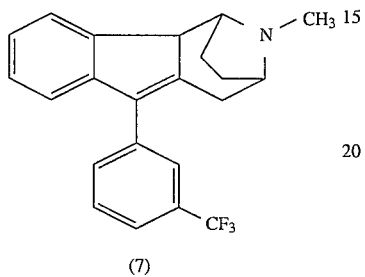

Preparation of 1 (SR):3(RS)-1,3-Ethano-2-methyl-5-(m-trifluoromethyl phenyl)-1,3,4,9b- tetrahydro-H-indeno[1,2-c] pyridine. HCl 0.75H$_2$O.

3.5 g of the compound (6) was dissolved in 69 ml of 12% HCl in ethanol and the solution was allowed to stand at room temperature overnight. It was then refluxed for 2.5 hours and allowed to cool. The solvent was evaporated off and the residue was treated with water, concentrated aqueous ammonia, and diethyl ether. The ether layer was separated and the aqueous layer was extracted again with diethyl ether. The ether extracts were combined and evaporated to an oil. This oil was dissolved in methanol and 0.8 mL of a 40% solution of Triton B in methanol was added. The solution was stirred at room temperature overnight. The solvent was removed by evaporation and the product was added to a mixture of diethyl ether and water. The ether layer was separated and filtered through a bed of silica gel. The diethyl ether was evaporated off and the resulting brown oil was dissolved in a small volume of ethanol. To the solution was added a slight excess of HCl in ethanol. The solution was diluted with about 200 ml of diethyl ether and was stored in the freezer. The resulting solid product was filtered off in the cold, washed with diethyl ether and dried to yield 2.18 g of the desired product, compound (7), as the HCl salt with 0.75 mole of water of crystallization, mp 183°–186° C. (Compound (7) has also been designated as compound L of the invention.)

Analysis Found C, 65.42; H, 5.78; N, 3.30; Cl, 8.34; F, 13.71 For C$_{22}$H$_{20}$NF$_3$.HCl Calcd: C, 65.18; H, 5.59; N, 3.46; Cl, 8.74; F, 14.06

Example 4a

Similarly prepared was compound J. A difference in the way that compound J was prepared as compared to the previous two examples was that the product was purified by chromatography of the free base on silica gel, eluting with methylene chloride then with increasing concentrations of methanol to 5%.

Example 4b

Compound S was also made in a similar manner. Differences in the way compound S was made are as follows: the carbinol proved difficult to convert completely to the eliminated product The mixture was separated by column chromatography eluting with increasing concentrations of ethanol up to 12.5% in methylene chloride. After evaporation of the fractions containing the product, the product was obtained as the free base.

Example 4c

Compound N was made in a similar manner. mp 126°–128° C.

Example 4d

Compound H was made in a similar manner. Differences in the way compound H was made are as follows: the crude product from the Triton B reaction was purified on a reversed-phase chromatography column (C18)in methanol. Subsequently, the fractions containing the desired product were further purified by reverse phase high pressure liquid chromatography (C18) ((RP-HPLC)(C18)) in methanol:water 90:10. The product was dissolved in excess HCl in methanol, evaporated and recrystallized from isopropanol, washed with methanol and dried in a vacuum desiccator. The HCl salt with 1.0 mole of water of crystallization had a m.p. of 160°–163° C.

Example 4e

Compound A was made in a similar manner.

The HCl salt with 0.5 mole of water of crystallization had a m.p. of 231°–3° C. with decomposition.

Example 4f

Compound G was prepared in an analogous manner to the examples above. The HCl salt with 0.5 mole of water of crystallization had amp of 138°–140° C. with decomposition.

Example 4g

Compound E was prepared in an analogous manner. mp153°–155° C. The HCl salt of Compound E with 1.0 mole of water of crystallization was also prepared and it had a melting point of 178°–180° C.;

EXAMPLE 5

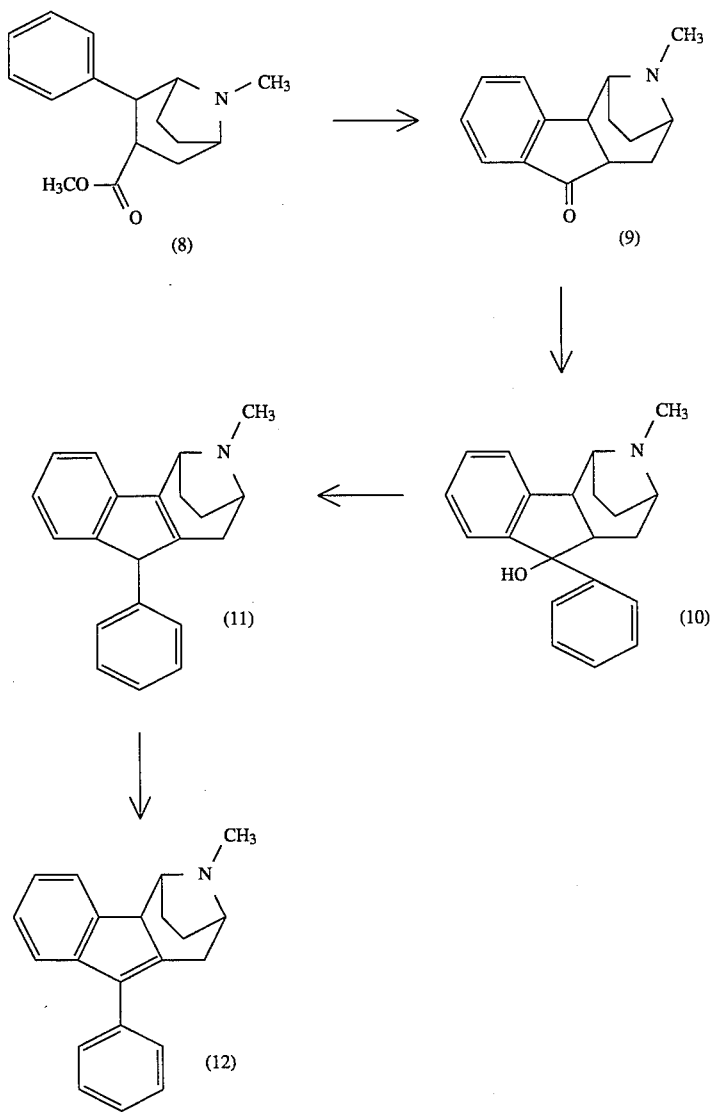

25 g of ester (8) was dissolved in 135 ml of 20% HCl and heated at reflux for 2 hours. The resulting reaction mixture was concentrated to a resin, and dried by azeotroping with 3×100 ml portions of benzene. The product was dried overnight in vacuo to give 27 g of crude material which was dissolved in 63 ml of thionyl chloride to give 34 g of a glassy product. This was allowed to stand for two days under 500 ml of ether, whereupon it solidified. Filtration and washing with ether gave 25 g of product.

This material was dissolved in 150 ml of $(CHCl_2)_2$ and treated at 40°–50° C. with 28 g of $AlCl_3$. The mixture was allowed to stir at 45° C. for two hours and then poured into 400 ml of cold 5% HCl. Ether was added, and the organic layer was separated. The aqueous layer was basified with 50% KOH, and extracted with three 300 ml portions of ether, which 10 were combined and evaporated to give 8.1 g of product (9) as an oil.

A solution of 3 g of the above product (9) in 10 ml of $CH_2Cl_2$ was added to a solution of phenyl magnesium bromide prepared from 0.95 g of magnesium and 6.3 g of bromobenzene in 15 ml THF and 10 ml of $CH_2Cl_2$ at –50° with stirring. The resulting solution was stirred for an additional hour while being allowed to warm to room temperature. It was then poured into a solution of 10 g of $NH_4Cl$ in 40 ml of ice-water. The resulting mixture was extracted with two 40 ml portions of $CH_2Cl_2$ which were combined, dried, and concentrated to an oil which crystallized on treatment with ether giving 3.7 g of product (10), m.p. 173°–175° C.

The above product (10) (3.6 g) was dissolved in 20 ml of approximately 10% ethanolic HCl and heated at reflux for 1 hour. The reaction mixture was concentrated to 10 ml, and the product allowed to crystallize by standing in the freezer. White crystals were obtained, which were filtered and recrystallized by dissolving in 15 ml methanol, adding ether to the cloud point, and cooling to give 1.9 g of hydrochloride salt, m.p. 202°–204° C. This was converted to the free base by treatment with dilute $NH_4OH$, extraction with ether, drying and concentration to give 1.05 g. of the base of the compound of formula (11), m.p. 117°–118° C.

Compound (11) (1.0 g) dissolved in 20 ml of ether was added to a suspension of sodium amide prepared from 320 mg of sodium in 50 ml of liquid anhydrous ammonia. The reaction mixture was allowed to warm to room temperature over 1 hour, replacing the evaporated ammonia with ether. Saturated NH₄Cl solution (20 ml) was added, the ether layer separated, and the aqueous layer extracted with fresh ether. The combined ether extracts were washed with water, dried over anhydrous K₂CO₃, and evaporated giving an oil which was recrystallized from hexane to give 450 mg of the compound of formula (12), m.p. 100°–102° C.

EXAMPLE 6

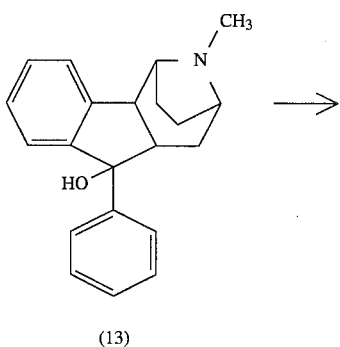

(13)

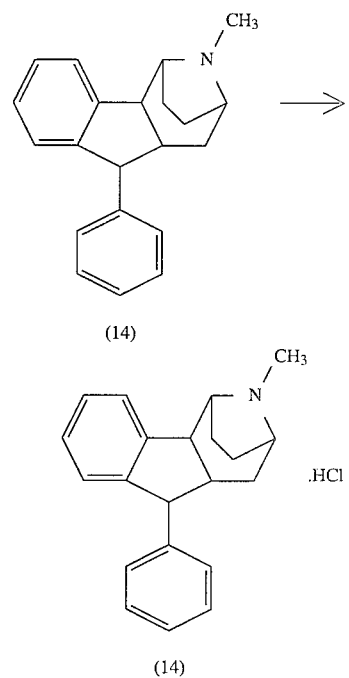

(14)

The compound (13) (6.5 m mole) and 2.4 g (65 m mole) NaBH₄ were ground together in a mortar and added in portions to 40 ml trifluoroacetic acid under N₂, with stirring at a rate to maintain the temperature below 5° C. The reaction mixture was allowed to stir at 0° for 15 minutes, then concentrated at 0° to remove most of the solvent. Ice water was added and the reaction mixture was basified in the cold with 10% NaOH. The reaction mixture was extracted with ether. The ether layer was concentrated to a colorless gum, 1.9 g.

EXAMPLE 7

1.8 g of the crude free base from, of the compound (14) was dissolved in acetone, filtered and treated with a slight excess of ethereal HCl. Fine prisms slowly formed. These were cooled, filtered, and dried in high vacuum for two days to obtain the hydrochloride of compound (14).

| Calc. | NC$_{21}$H$_{23}$HCl | Micro Anal. | Theory | Found |
|---|---|---|---|---|
| M.W. | 325.86 | Carbon | 77.40 | 77.26 |
| M.P/B.P. | 288–289° Dec. | Hydrogen | 7.11 | 7.15 |
|  |  | Nitrogen | 4.30 | 4.11 |
|  |  | Chlorine m/e-289 | 10.88 | 11.23 |

EXAMPLE 8

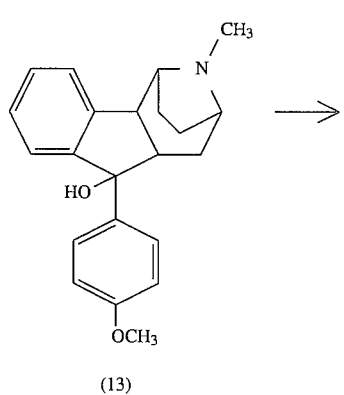

(13)

-continued

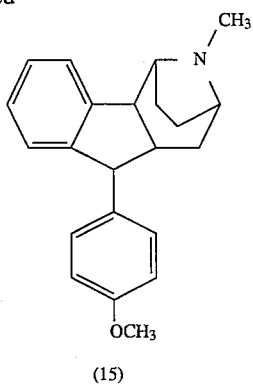

(15)

The compound (13) was mixed with 2.4 g NaBH₄ and added in portions to 40 ml trifluoroacetic acid with stirring under N₂, at a rate to control frothing and maintain temperature at 0°–5° C. for 30 minutes. The mixture (cloudy solution) was allowed to stir at 0° for 15 minutes concentrated at room temperature to remove most of solvent. Ice water was added and the reaction mixture was basified in the cold with concentrated NaOH. The reaction mixture was extracted with ether. Washed The ether extracts were washed with brine, dried K₂CO₃ and concentrated to an oil, 1.9 g, to obtain the compound (15).

EXAMPLE 9

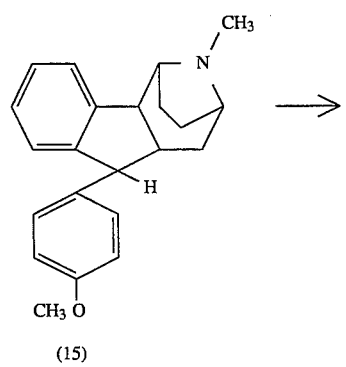

(15)

→

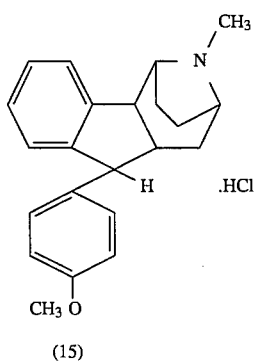

(15)

The crude oily product of the previous example which was compound (15), was dissolved in 30 ml acetone and treated with a slight excess of ethereal HCl. A white crystalline solid (the hydrochloride of the compound (15)) slowly precipitated. It was cooled and filtered, 1.3 g, mp: 190°–192°.

| Calc. | $C_{22}H_{25}NO$ HCl | Micro Anal. | Theory | Found |
|---|---|---|---|---|
| M.W. | 355.908 | Carbon | 74.24 | 66.98 |
| M.P/B.P | 190–92° | Hydrogen | 7.36 | 6.85 |
| | | Nitrogen | 3.93 | 3.41 |
| | | Chlorine | 9.96 | 17.30 |
| | | m/e = 319 | | |

What is claimed is:

1. A compound of the formula

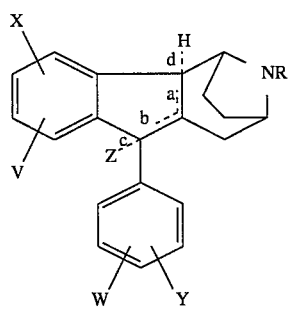

I wherein R is H; $(C_1-C_8)$alkyl; $(C_3-C_8)$cycloalkyl; $(C_3-C_8)$cycloalkyl$(C_1-C_8)$alkyl; $(C_3-C_8)$alkenyl; and $(C_3-C_8)$alkynyl; with the proviso that the double bond in $(C_3-C_8)$alkenyl and the triple bond in $(C_3-C_8)$alkynyl must be separated from the nitrogen in the 2-position by at least one saturated carbon;

X, V, W and Y are each independently H, halogen, $NO_2$, CN, $(C_1-C_8)$alkyl, $O(C_1-C_8)$-alkyl, $S(C_1-C_8)$alkyl, $(C_3-C_8)$alkenyl; $(C_3-C_8)$alkynyl; hydroxy$(C_1-C_8)$alkyl; cyano$(C_1-C_4)$alkyl; $S(O)_m(C_1-C_8)$-alkyl wherein m is 1 or 2; $NH_2$, OH, or $CF_3$; or W and Y on adjacent carbons may be

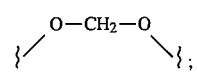

and a, b, c, and d are optionally chemical bonds with the proviso that when a is a bond, b is not a bond, c is a bond, d is not a bond, and Z is H;

and when b is a bond, a is not a bond, c is not a bond, and d is a bond;

and when a and b are not bonds, and c and d are bonds and Z is H or OH;

and when d is a bond, said bond is attached to H, and when d is not a bond, said H is not present;

and when c is not a bond, Z is not present;

or a stereoisomer thereof;

or a pharmaceutically acceptable salt thereof.

2. A compound according to claim 1 of the formula

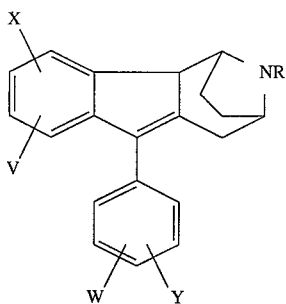

I''' wherein R is H; $(C_1-C_8)$alkyl; $(C_3-C_8)$cycloalkyl; $(C_3-C_8)$cycloalkyl$(C_1-C_8)$alkyl; $(C_3-C_8)$alkenyl; and $(C_3-C_8)$alkynyl, with the proviso that the double bond in $(C_3-C_8)$alkenyl and the triple bond in $(C_3-C_8)$alkynyl must be separated from the nitrogen in the 2-position by at least one saturated carbon;

X, V, W and Y are each independently H, halogen, $NO_2$, CN, $(C_1-C_8)$alkyl, $O(C_1-C_8)$-alkyl, $S(C_1-C_8)$alkyl, $(C_3-C_8)$alkenyl; $(C_3-C_8)$alkynyl; hydroxy$(C_1-C_8)$alkyl; cyano$(C_1-C_4)$alkyl; $S(O)_m(C_1-C_8)$alkyl wherein m is 1 or 2; $NH_2$, OH, or $CF_3$; or W and Y on adjacent carbons may be

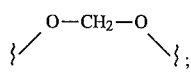

or a pharmaceutically acceptable salt thereof.

3. A compound according to claim 1 of the formula

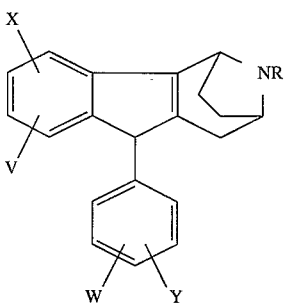

I'' wherein R is H; $(C_1-C_8)$alkyl; $(C_3-C_8)$cycloalkyl; $(C_3-C_8)$cycloalkyl$(C_1-C_8)$alkyl; $(C_3-C_8)$alkenyl; and $(C_3-C_8)$alkynyl, with the proviso that the double bond in $(C_3-C_8)$alkenyl and the triple bond in $(C_3-C_8)$alkynyl must be separated from the nitrogen in the 2-position by at least one saturated carbon;

X, V, W and Y are each independently H, halogen, $NO_2$, CN, $(C_1-C_8)$alkyl, $O(C_1-C_8)$-alkyl, $S(C_1-C_8)$alkyl, $(C_3-C_8)$alkenyl; $(C_3-C_8)$alkynyl; hydroxy$(C_1-C_8)$alkyl; cyano$(C_1-C_4)$alkyl; $S(O)_m(C_1-C_8)$alkyl wherein m is 1 or 2; $NH_2$, OH, or $CF_3$; or W and Y on adjacent carbons may be

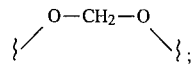

or a pharmaceutically acceptable salt thereof.

4. A compound according to claim 1 of the formula

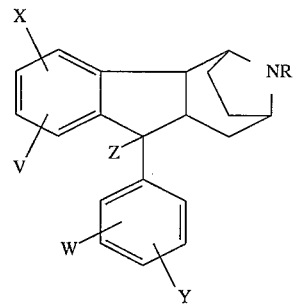

I$^{IV}$ wherein R is H; $(C_1-C_8)$alkyl; $(C_3-C_8)$cycloalkyl; $(C_3-C_8)$cycloalkyl$(C_1-C_8)$alkyl; $(C_3-C_8)$alkenyl; and $(C_3-C_8)$alkynyl, with the proviso that the double bond in $(C_3-C_8)$alkenyl and the triple bond in $(C_3-C_8)$alkynyl must be separated from the nitrogen in the 2-position by at least one saturated carbon;

X, V, W and Y are each independently H, halogen, $NO_2$, CN, $(C_1-C_8)$alkyl, $O(C_1-C_8)$-alkyl, $S(C_1-C_8)$alkyl, $(C_3-C_8)$alkenyl; $(C_3-C_8)$alkynyl; hydroxy$(C_1-C_8)$alkyl; cyano$(C_1-C_4)$alkyl; $S(O)_m(C_1-C_8)$alkyl wherein m is 1 or 2; $NH_2$, OH, or $CF_3$; or W and Y on adjacent carbons may be

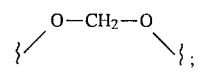

Z is H or OH;

or a pharmaceutically acceptable salt thereof.

5. A compound according to claim 1 wherein R is H.

6. A compound according to claim 1 wherein R is $CH_3$.

7. A compound according to claim 1 wherein W is H and Y is —$OCH_3$.

8. A compound according to claim 1 wherein no more than one of X, V, W and Y is halogen.

9. A compound of formula I according to claim 1 with the proviso that when Z is OH, b and a are not bonds, and at least one of X and V are halogen; then neither W nor Y may be $O(C_1-C_8)$alkyl, in the 4'-position.

10. A compound according to claim 1, selected from the group consisting of

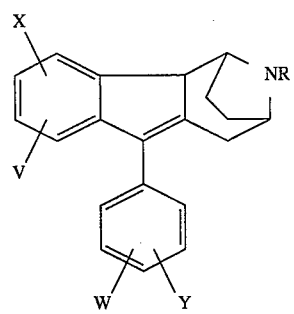

I'''

| Compd | X | V | W | Y | R |
|---|---|---|---|---|---|
| A | 7'-F | H | H | 4'-Cl | CH₃ |
| B | H | H | H | 4'-OCH₃ | H |
| C | H | H | H | 4'-Cl | CH₃ |
| D | H | H | H | 5'-Cl | CH₃ |
| E | 7-Cl | H | H | 4'-F | CH₃ |
| F | H | H | H | 4'-SCH₃ | CH₃ |
| G | 7-F | H | H | 5'-F | CH₃ |
| H | 7-F | H | H | 4'-F | CH₃ |
| I | 7-F | H | H | H | CH₃ |
| J | H | H | H | 4'-CH₃ | CH₃ |
| K | H | H | H | 4'-F | CH₃ |
| L | H | H | H | 5'-CF₃ | CH₃ |
| M | 8-F | H | H | H | CH₃ |
| N | H | H | 4'-Cl | 5'-CF₃ | CH₃ |
| O | H | H | H | 5'-F | CH₃ |
| P | 8-F | H | H | 5'-F | CH₃ |
| Q | H | H | H | H | H |
| R | H | H | H | 4'-OCH₃ | CH₃ |
| S | H | H | 2'-CF₃ | H | CH₃ |
| T | H | H | H | H | CH₃ |
| U | H | H | H | H | CH₃ |
| V | 7-OCH3 | H | H | H | CH₃ | or a pharmaceutically acceptable salt thereof.

11. A compound according to claim 1, selected from the group consisting of:

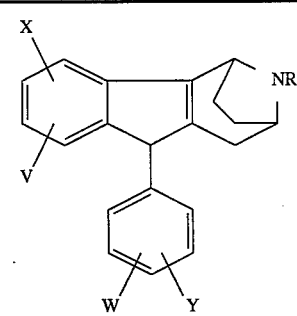

I''

| Compd | X | V | W | Y | R |
|---|---|---|---|---|---|
| W | H | H | H | 4'-F | CH₃ |
| X | H | H | H | 4'-OCH₃ | H |
| Y | H | H | H | 4'-OCH₃ | CH₃ |
| Z | 8-OCH₃ | H | H | H | CH₃ |
| AA | H | H | 4'-OCH₃ | 5'-OCH₃ | CH₃ |
| BB | 7-OH | H | H | H | CH₃ |
| EE | 7-OCH₃ | H | H | H | CH₃ |
| FF | 7-OCH₃ | H | H | H | H | or a pharmaceutically acceptable salt thereof.

12. A compound according to claim 1, selected from the group consisting of:

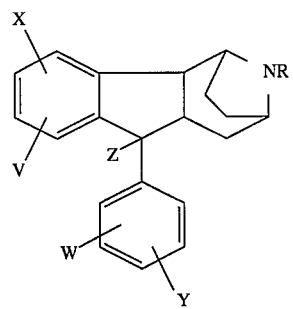

I^IV

| Compd | X | V | W | Y | Z | R |
|---|---|---|---|---|---|---|
| GG | H | H | H | 4'-OCH₃ | H | CH₃ |
| HH | H | H | H | 4'-Cl | OH | CH₃ |
| II | 7-Cl | H | H | 4'-F | OH | CH₃ |
| JJ | H | H | H | 4'-OCH₃ | OH | H |
| KK | H | H | H | 4'-SCH₃ | OH | CH₃ |
| LL | 8-Cl | H | H | 4'-F | OH | CH₃ |
| MM | H | H | H | H | H | CH₃ |
| NN | H | H | H | 5'-CF₃ | OH | CH₃ |
| OO | H | H | H | 4'-CH₃ | OH | CH₃ |
| PP | H | H | H | 4'-OCH₃ | OH | CH₃ |
| QQ | H | H | H | 5'-Cl | OH | CH₃ |
| RR | H | H | H | 5'-F | OH | CH₃ |
| SS | H | H | H | 4'-F | OH | CH₃ |
| TT | H | H | H | 2'-CF₃ | OH | CH₃ |
| UU | 8-OCH₃ | H | H | H | OH | CH₃ |
| VV | 8-Cl | H | H | H | OH | CH₃ |
| WW | H | H | —* | 4'5'-OCH₂O— | OH | CH₃ |
| XX | 7-Cl | H | H | 4'-OCH₃ | OH | CH₃ |
| YY | 7-Cl | H | H | H | OH | CH₃ |
| ZZ | 8-Cl | H | H | 4'-OCH₃ | OH | CH₃ |
| AAA | H | H | H | H | OH | CH₃ |
| BBB | 6-Cl | H | H | 4'-OCH₃ | OH | CH₃ |
| CCC | 7-F | H | H | 4'OCH₃ | OH | CH₃ |
| DDD | 7-OCH₃ | H | H | H | OH | CH₃ |

*In the case of compound WW, W and Y together are 4'5'-OCH₂O—.

or a pharmaceutically acceptable salt thereof.

13. The compound according to claim 1 of the formula

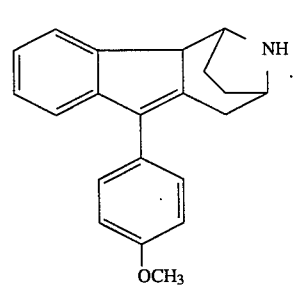

or a pharmaceutically acceptable salt thereof.

14. A pharmaceutical composition for treating patients afflicted with depression which comprises an anti-depressive effective amount of a compound according to claim 1 and a pharmaceutically acceptable carrier therefor.

15. A pharmaceutical composition for treating patients afflicted with allergy or bronchoconstriction which comprises an anti-allergy or anti-bronchoconstriction effective amount of a compound according to claim 1 and a pharmaceutically acceptable carrier therefor.

16. A pharmaceutical composition for treating patients afflicted with tumors which comprises an anti-tumor effective amount of a compound of formula of claim 9 and a pharmaceutically acceptable carrier therefor.

17. A method of treating a patient afflicted with an allergy or bronchoconstriction which comprises administering to said patient an anti-allergy or anti-bronchoconstriction effective amount of a compound according to claim 1.

* * * * *